(12) United States Patent
Zeng et al.

(10) Patent No.: US 10,978,177 B2
(45) Date of Patent: Apr. 13, 2021

(54) METHOD FOR AUTOMATICALLY AND EFFICIENTLY FITTING REPULSIVE POTENTIALS THROUGH DFTB (71) Applicant: SHENZHEN JINGTAI TECHNOLOGY CO., LTD., Guangdong (CN)

(72) Inventors: Qun Zeng, Guangdong (CN); Peiyu Zhang, Guangdong (CN); Yingdi Jin, Guangdong (CN); Jian Ma, Guangdong (CN); Lipeng Lai, Guangdong (CN); Shuhao Wen, Guangdong (CN)

(73) Assignee: SHENZHEN JINGTAI TECHNOLOGY CO., LTD., Guangdong (CN)

( * ) Notice: Subject to any disclaimer, the term of this patent is extended or adjusted under 35 U.S.C. 154(b) by 1 day.

(21) Appl. No.: 16/482,704

(22) PCT Filed: May 11, 2018

(86) PCT No.: PCT/CN2018/086599
§ 371 (c)(1),
(2) Date: Jul. 31, 2019

(87) PCT Pub. No.: WO2019/134325
PCT Pub. Date: Jul. 11, 2019

(65) Prior Publication Data
US 2020/0312427 A1    Oct. 1, 2020

(51) Int. Cl.
*B82B 1/00* (2006.01)
*G16C 10/00* (2019.01)
(52) U.S. Cl.
CPC .................. *G16C 10/00* (2019.02)

(58) Field of Classification Search
CPC ........ G16C 10/00; G16C 99/00; G16C 20/50; G16C 20/70; G16C 20/00
See application file for complete search history.

(56) References Cited

FOREIGN PATENT DOCUMENTS

CN    105787273    7/2016
CN    106372400    2/2017

OTHER PUBLICATIONS

J.M. Knaup, B. Hourahine, Th. Frauenheim; "Initial Steps toward Automating the Fitting of DFTB Erep (r)," 2007, American Chemical Society, pp. 5637-5641. (Year: 2007).*

(Continued)

*Primary Examiner* — Mohamed Charioui
*Assistant Examiner* — Christine Y Liao
(74) *Attorney, Agent, or Firm* — JCIP Global Inc.

(57) ABSTRACT

A method for automatically and efficiently fitting repulsive potentials through DFTB includes: optimizing a molecule containing an atomic pair, and performing spacing scan on the atomic pair according to an acting interval of repulsive potentials; performing high-accuracy energy calculation on a scanning result; performing difference calculation on obtained energy to obtain second-order derivatives of force and energy; saving a structure, the energy, the second-order derivatives of force and energy into a database; acquiring energy without a repulsive potential as well as the second-order derivatives of force and energy to obtain target values of the repulsive potentials; transforming the separated target values of the repulsive potentials into splines; splicing multiple splines on a mean position between equilibrium position points to obtain new train data; constructing a train set by means of necessary samples and choosable samples; and fitting the repulsive potentials through singular value decomposition.

7 Claims, 5 Drawing Sheets

(56) References Cited

OTHER PUBLICATIONS

Michael Gaus, Chien-Pin Chou, Henryk Witek and Marcus Elstner, "Automatized Parametrization of SCC-DFTB Repulsive Potentials: Application to Hydrocarbons," 2009, American Chemical Society, pp. 11866-11881. (Year: 2009).*

Benjamin Lynch; "Introduction to Gaussian 09;" Nov. 24, 2009; Supercomputing Institute for Advanced Computational Research; pp. 1-75. (Year: 2009).*

"International Search Report (Form PCT/ISA/210) of PCT/CN2018/086599," dated Jan. 30, 2019, with English translation thereof, pp. 1-4.

Zoltán Bodrog, et al., "Automated Repulsive Parametrization for the DFTB Method," Journal of Chemical Theory and Computation, Jul. 2011, pp. 2654-2664.

* cited by examiner

METHOD FOR AUTOMATICALLY AND EFFICIENTLY FITTING REPULSIVE POTENTIALS THROUGH DFTB

CROSS-REFERENCE TO RELATED APPLICATION

This application is a 371 of international application of PCT application serial no. PCT/CN2018/086599, filed on May 11, 2018. The entirety of the abovementioned patent application is hereby incorporated by reference herein and made a part of this specification.

BACKGROUND OF THE INVENTION

1. Technical Field

The invention belongs to a biological information technology, and relates to functional material design, in particular to a method for automatically and efficiently fitting repulsive potentials through DFTB.

2. Description of Related Art

DFTB is a rapid calculation-based high-accuracy quantum chemistry method which fulfills effective equilibrium of the calculation scale and accuracy and has been widely applied in the fields of bioprotein simulation, functional material design and the like. A repulsive potential is an important constituent part of a DFTB parameter, and the reliability of the repulsive potential has a great influence on the accuracy of calculation simulation.

According to an existing DFTB parametrization scheme, a repulsive potential curve is determined by manually constructing a train set and performing spline fitting by means of a large quantity of trained sample points; and due to the fact that multiple bonding forms of two atomic pairs need to be described by the same repulsive potential, if fitting based on the large quantity of the trained sample points cannot accurately cover different bonding forms, for example, C . . . O have two bonding forms C—O/C═O under interaction, and equilibrium positions of the two bonding forms are obviously different, so that two bond lengths cannot be equilibrated through direct spline fitting.

The spline fitting can fit only one atomic pair curve every time, has an obvious fitting sequence, has very high requirements for the complexity of a train set and may cause the problems of compatibility and matching of fitted repulsive potentials, for example, for the sake of O . . . O interaction, H—H and O—H repulsive potentials should be prepare in advance; however, whether or not the developed O—O interaction is suitable for a system except these three actions reminds uncertain, and repeated iteration of a development parameter process can be caused, so that the development speed is low; and such fitting involves the construction of a large quantity of train sets and test sets, parameter adjustment and test calibration, and thus, a large amount of manual intervention is needed.

BRIEF SUMMARY OF THE INVENTION

In order to overcome the defects of the prior art, the invention provides a method for automatically and efficiently fitting repulsive potentials through DFTB based on a differential evolution algorithm. The method includes the following steps:

(1): generating a saturated molecule with hydrogens for a target atomic pair according to the information of atoms, and optimizing a molecule by means of a high-accuracy density functional theory (DFT) method, such as B3LYP/cc-pVTZ and PBE0/cc-pVTZ methods in Gaussian09 quantum chemistry software; and performing spacing scan on an atomic pair through a DFT method at same accuracy according to an acting interval of repulsive potentials.

(2): performing high-accuracy energy calculation on the spacing san through a high-accuracy method, such as G3B3 and CCSD/CBS methods, in Gaussian09 software and other software;

(3): performing difference calculation on energy obtained through the high-accuracy method to obtain second-order derivatives of force and energy;

(4): saving the energy obtained by calculating a structure through the high-accuracy method as well as the second-order derivatives of force and energy into a data base;

(5): acquiring a difference between a calculation result obtained through a high-accuracy method and energy without a repulsive potential as well as second-order derivatives of force and energy which are obtained by calculating the structure by means of DFTB+ and other procedures which can fulfill DFTB calculation to obtain fitted target values of the repulsive potentials;

(6): performing spline interpolation according to an atomic spacing and target values of the repulsive potentials to obtain multiple splines, and transforming separated energy samples into continued energy curves;

(7): setting a mean position between equilibrium position points as a splice point, determining end point energy as 0.0 according to a fitting end point, and splicing the multiple splines on division points in a reverse order from the fitting end point to obtain new train energy data;

(8): constructing a train set pool by choosing two points closest to a starting point and an end point of a target repulsive potential as well as the equilibrium position points as necessary sample points and by choosing 2-3 sample points close to a fitting starting point as supplementary sample points; and (9): performing fitting by means of a singular value decomposition scheme to obtain an initial repulsive potential, then transforming the initial repulsive potential into a standard repulsive potential through a method for fitting the initial repulsive potential, and performing testing and validation by means of the standard repulsive potential.

The above technical scheme adopted by the invention has the advantage of determining division points on the basis of a differential evolution algorithm by means of equilibrium bond length points and a small quantity of sample points to jointly fit multiple repulsive potential curves.

Figure 5:
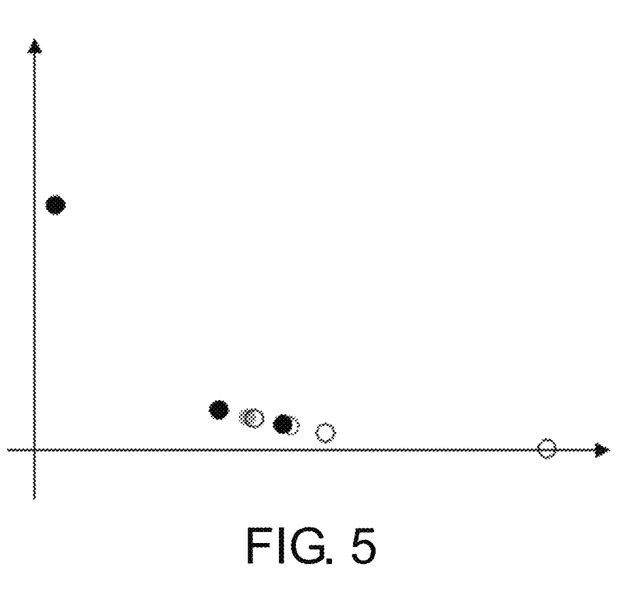
FIG. 5 is one embodiment of the invention, in which a starting point, and end point and equilibrium positions are chosen as necessary sample points, and 2-3 samples close to the equilibrium positions are chosen as supplementary samples.

In order to ensure fitting effect, except division points normally divided in bond type areas, 1-2 train samples and corresponding division points need to be inserted, and the choosing of the division points impacts the fitting effect to a certain degree, and thus the division points need to be optimized. The differential evolution algorithm is adopted to optimize train sets and the division points and includes the following steps:

A: initializing division points and separation points by means of mean positions of starting point-equilibrium point, equilibrium point-equilibrium point and equilibrium point-end point, wherein at least one division point is contained from one equilibrium point to one equilibrium point, as shown in FIG. 5;

B: randomly extracting 1-2 supplementary samples from the train set pool according to density of the samples and the division points to maintain that at least one sample within a separation point interval, and performing transverse perturbation without going beyond necessary samples on the division points to generate 15-50 individuals;

C: performing quadratic fitting on each individual, that is to say, fitting the initial repulsive potential and the target repulsive potential, and validating an evaluation error: for the first time, linear fitting is performed on random or evolved separated points to obtain the initial repulsive potential; division points are uniformly divided to obtain energy and second derivatives of force and energy of the initial repulsive potential, and the linear fitting is performed to obtain the target repulsive potential; and calculation is performed by means of the repulsive potentials obtained through fitting, and relative energy and structural similarity are taken as grading functions to evaluate the fitting every time.

D: generating separation point perturbation and sample perturbation through the differential evolution algorithm; sequencing filling in each generation according to a grading evaluation value, and acquiring a difference between an optimal individual vector and other individual vectors by taking the division points and the supplementary sample points as one vector to generate a vector in a perturbation direction; performing perturbation in multiple perturbation directions on other vectors to generate new division points and supplementary samples; if the new division points are beyond a border, randomly generating a division point which meets a condition; and if the new supplementary samples are not within a train set, randomly extracting one of the supplementary samples contained in the train set as a new supplementary sample; and E: iterating step C-D till errors are converged.

The method has the following advantages:

1. Due to the fact that the equilibrium positions of different bond types are mainly adopted, while energy and force and only adopting a small quantity of sample points for assisting the fitting in a fitting process, the information of the equilibrium positions is primarily retained, and the weights of the equilibrium positions are approximately equal, so that the problem of disequilibrium of bond types in fitting is solved.

2. Due to the fact that fitting is performed in a form of linear equations, the fitting of multiple repulsive potentials can be taken into one set of linear equations together to be realized, so that the problem of parameter compatibility is solved.

3. Automatic fitting of the repulsive potentials is realized by means of the differential evolution algorithm and the database.

DETAILED DESCRIPTION OF THE INVENTION

Preferred embodiments of the invention are detailed as follows in combination with the drawings.

Embodiment 1

Figure 1:
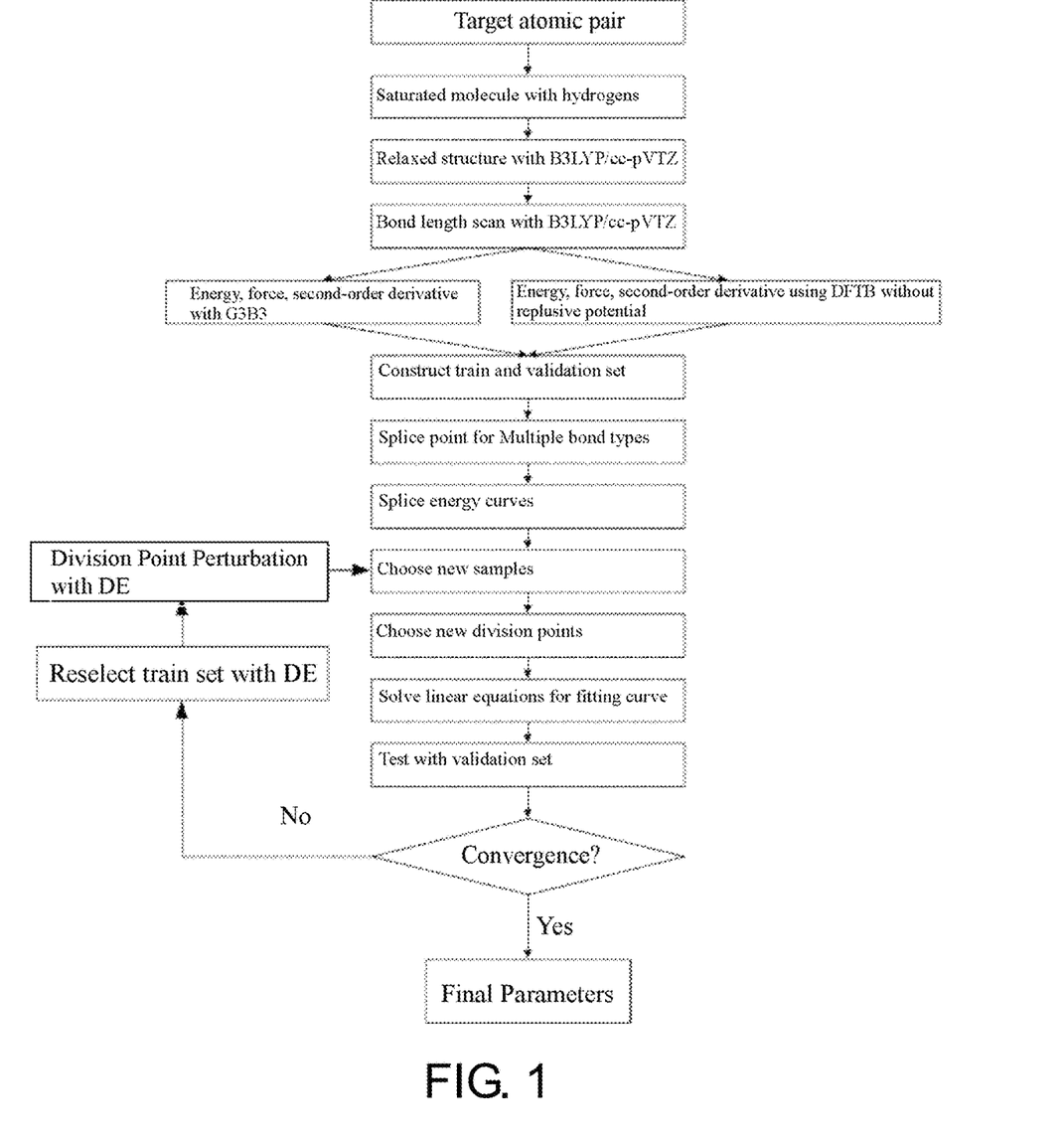
FIG. 1 is a flow chart of a method for automatically and efficiently fitting repulsive potentials through DFTB of the invention.
Figure 2:
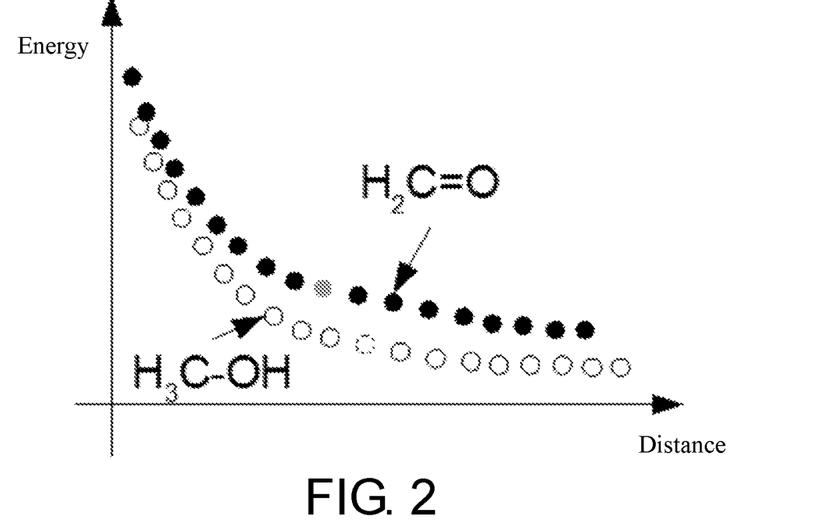
FIG. 2 is one embodiment of the invention, in which a C—O atomic spacing VS repulsive potential energy sample is obtained by scanning C . . . O bond types, wherein black dots are H2C=O (grey represents an equilibrium position), and circles are H3C—HO (a dashed circle is an equilibrium position).
Figure 3:
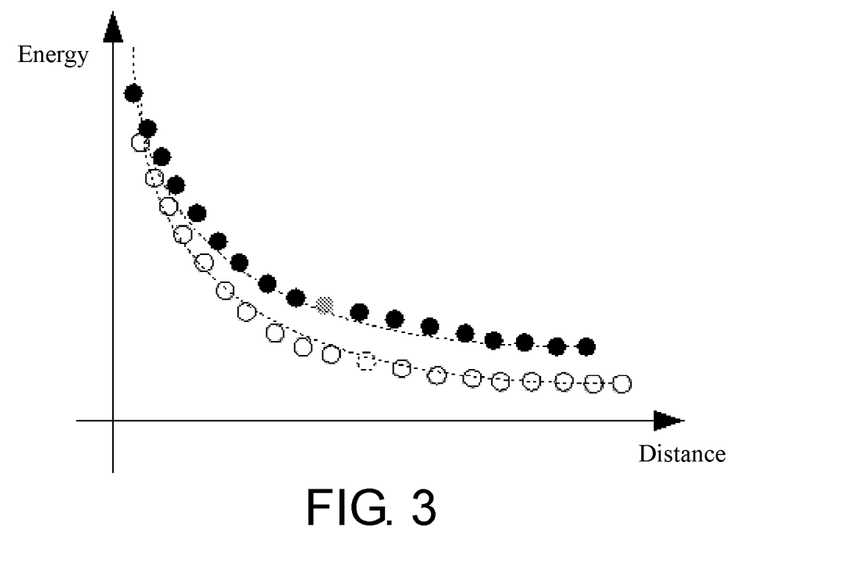
FIG. 3 is one embodiment of the invention, in which a spline corresponding to C . . . O bond types is obtained through fitting.
Figure 4:
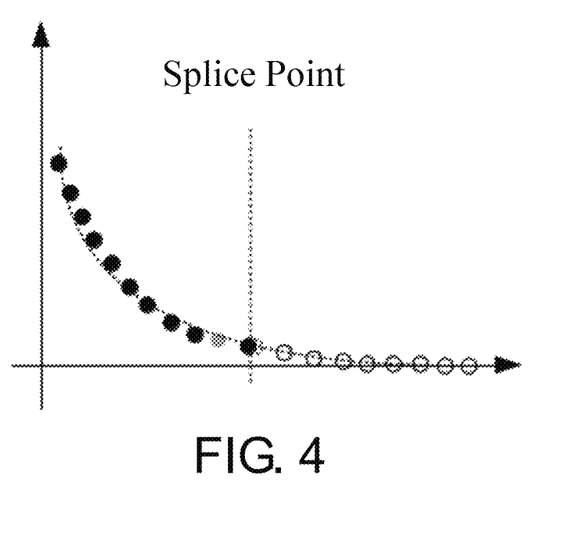
FIG. 4 is one embodiment of the invention, in which C . . . O bond splines are spliced into one spline, two bond types are equilibrated, and a train set is constructed by choosing two points closest to a starting point and an end point of a target repulsive potential as well as equilibrium position points as necessary sample points and by choosing 2-3 sample points close to a fitting starting point as supplementary sample points.

As shown in FIG. 1, the method for fitting the repulsive potentials through a differential evolution algorithm includes the following steps:

(1): a saturated molecule with hydrogens is generated for a target atomic pair according to the information of atoms, and a molecular pair is optimized by means of a B3LYP/cc-pVTZ method in Gaussian09; and spacing scan is performed on the atomic pair by means of the B3LYP/cc-pVTZ method according to an acting interval of repulsive potentials;

(2): high-accuracy energy calculation is performed on the spacing scan through G3B3 in Gaussian09;

(3): difference calculation is performed on energy obtained through a G3B3 method to obtain second derivatives of force and energy;

(4): the energy obtained by calculating a structure through the G3B3 method as well as the second derivatives of force and energy are saved into a database;

(5): the difference between the G3B3 result and the energy without a repulsive potential as well as the second-order derivatives of force and energy which are obtained by calculating the structure through DFTB+ and other procedures capable of performing DFTB calculation to is acquired to obtain corresponding values of the repulsive potentials;

(6): as shown in FIG. 2, in which a C—O atomic spacing VS repulsive potential energy sample is obtained by scanning C . . . O bond types, wherein black dots are H2C=O (grey represents an equilibrium position), and circles are H3C—HO (a dashed circle is an equilibrium position); spline interpolation is performed according to scanning results of multiple bond types to obtain multiple splines, and separated energy samples are transformed into continuous energy curves to facilitate the mergence of energy curves as well as the fitting of multiple bond types;

(7): as shown in FIG. 3, fitting is performed to obtain splines which correspond to C . . . O bond types, a mean position between equilibrium position points is set as a splice point, end point energy is determined as 0.0 according to the position of a fitting end point, and the multiple splines on division points are spliced in a reverse order from the fitting end point to obtain new train energy data; multiple bond types are initially processed; as shown in FIG. 4, C . . . O bond splines are spliced into one spline, and two bond types are equilibrated;

(9): a train set pool is constructed by choosing two points closest to a starting point and an end point of a target repulsive potential as well as the equilibrium position points as necessary sample points and by choosing 2-3 sample points close to a fitting starting point as supplementary sample points.

As shown in FIG. 5, the starting point, the end point and the equilibrium positions are chosen as necessary sample points, and the 2-3 samples close to the equilibrium positions are chosen as supplementary samples.

The form of an initial repulsive potential curve $$(V_{AB}^{rep}(r))$$

is defined as a multi-section second-order continued derivable quartic polynomial, wherein an expression of the $i^{th}$ section is as follows: $S_{ABi}(r)=\Sigma_{k=0}^{4}s_{ABik}(r-r_{ABi})^k$.

Wherein A and B are elements corresponding to atoms of the atomic pair, k is power of number, i is atomic spacing r corresponds to a division interval sequence, $s_{ABik}$ is a coefficient of kth polynomial in an $i^{th}$ interval, and $r_{ABi}$ is a starting point of the $i^{th}$ interval. Thus, repulsive energy ($E^{rep}$) of a whole system can be expressed as follows:

$$E^{rep} = \sum_{a,b>a} V_{ab}^{rep}(r_{ab}) = \sum_{a,b>a} \sum_{k=0}^{4} s_{E_a E_b ik}(r_{ab} - r_{E_a E_b i})^k$$

Namely, a repulsive potential polynomial corresponding to an element Ea and an element Eb of an atom a and an atom b in the system is selected, a division interval i is determined according to an atomic spacing rab, and then the repulsive energy is obtained through calculation;

Similarly, a repulsive force expression of the atom a is as follows:

$$F_a^{rep} = -\sum_{b \neq a} \frac{r_a - r_a}{r_{ab}} \frac{dV_{ab}^{rep}}{dr}\bigg|_{r=r_{ab}}$$

Wherein $$\frac{dV_{ab}^{rep}}{dr}\bigg|_{r=r_{ab}} = \sum_{a,b>a} \sum_{k=0}^{4} k \times s_{E_a E_b ik}(r_{ab} - r_{E_a E_b i})^{k-1}$$

Fitting can be expressed in a form of a linear equation: M·s=b according to the expression of an initial repulsive potential, wherein M is a matrix determined the form of a multi-section polynomial, second-order continued derivable information on division points and sample point information, s is a vector determined by all parameters to be fitted, b is values of energy, a derivative and a second derivative which correspond to the second-order continued derivable information and the sample point information.

The follow equation is obtained according to a continued derivable value (cont) of repulsive potentials and fitting values (fit) of sample points:

$$\begin{bmatrix} M^{cont} \\ M^{fit} \end{bmatrix} \cdot s = \begin{bmatrix} 0 \\ b^{fit} \end{bmatrix}$$

Wherein Mcont is a matrix only containing the second-order continued derivable information on division points, Mfit is a matrix only containing the sample point information, bfit is vectors, only containing the sample point information, of values of energy, a derivative and a second derivative. Due to matrix transformation and continued derivability, bcont is a 0 vector. Furthermore, an s vector is disassembled into a necessary accurate fitting part (expl) determined by a sample point interval as well as other parts (other) according to accurate fitting:

$$M^{contother}s^{contother}+M^{contexpl}s^{contexpl}=0$$

$$M^{fitother}s^{fitother}+M^{fitexpl}s^{fitexpl}=b^{fit}$$

The above two equations are transformed and merged to obtain the following equation:

$$M^{last} \cdot s^{expl}=b^{fit}$$

An initial parameter is obtained through fitting by means of a singular value decomposition scheme; as the form of the initial repulsive potential is different from a final form to a certain degree, the initial repulsive potential is further transformed into a standard repulsive potential by means of a fitting method of the initial repulsive potential (quadratic fitting), and testing and verification are performed by means of the standard repulsive potential.

Figure 6:
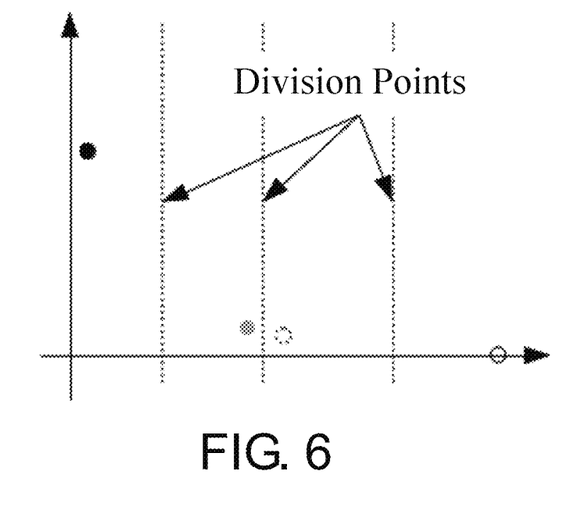
FIG. 6 is one embodiment of the invention, in which division points are initialized.
Figure 7:
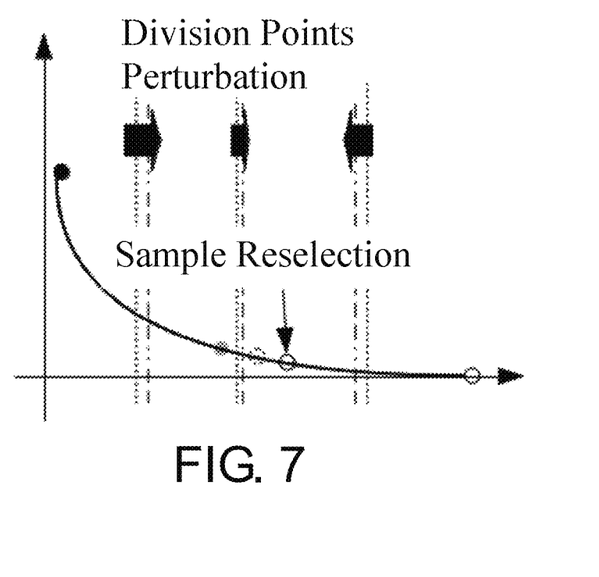
FIG. 7 shows that a fitting interval is divided into four intervals according to the number of the necessary sample points in FIG. 5, wherein a sample close to a equilibrium position is randomly added to a third interval, and division points are horizontally moved.
Figure 8:
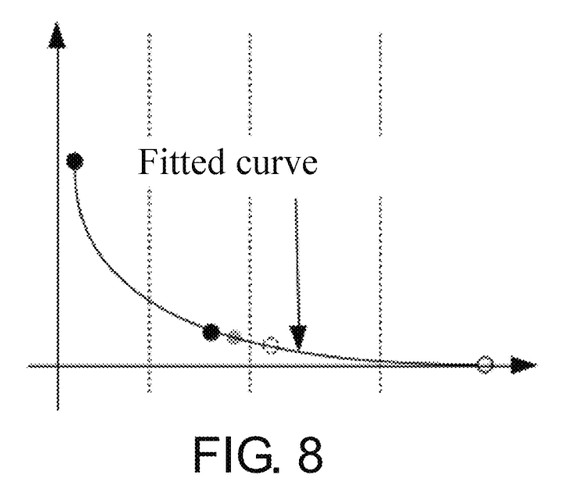
FIG. 8 is one embodiment of the invention, in which an initial repulsive potential is obtained through fitting based on linear equations.
Figure 9:
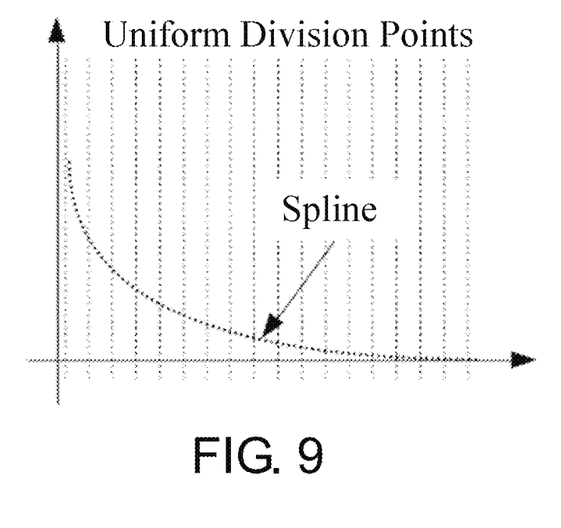
FIG. 9 is one embodiment of the invention, in which division points are uniformly divided.

In order to ensure the fitting effect, besides division points normally divided in bond type areas, 1-2 train samples and corresponding division points need to be inserted, and the choosing of the division points impacts the fitting effect to a certain degree, and thus the division points need to be optimized. The differential evolution algorithm is adopted to optimize train sets and the division points and includes the following steps:

A: division points and separation points are initialized by means of mean positions of starting point-equilibrium point, equilibrium point-equilibrium point and equilibrium point-end point, and at least one division point exists from one equilibrium point to one equilibrium point, as shown in FIG. 6;

B: 1-2 supplementary samples are randomly extracted from a train set pool according to the density of the samples and the division points to maintain at least one sample within a separation point interval, and transverse perturbation without going beyond necessary samples is performed on the division points to generate 20 individuals;

C: quadratic fitting is performed on each individual, that is to say, the initial repulsive potential and the target repulsive potential are fitted, and an evaluation error is validated: for the first time, linear fitting is performed on random or evolved separated points to obtain the initial repulsive potential; as shown in FIG. 7, a fitting interval is divided into four intervals according to the number of necessary sample points in FIG. 6, a sample close to an equilibrium position is randomly added to a third interval, and the division points are horizontally moved; then the initial repulsive potential is transformed into a spline, then the fitting interval is uniformly divided by selecting 0.02-0.05 Bohr as a spacing according to the distance from a starting point to an end point as well as actual situations, spline data is transformed into linear equations, and the linear equations are solved to obtain a target repulsive potential curve, as shown in FIG. 8;

As shown in FIG. 9, division points are uniformly divided as follows: calculation is performed by means of a repulsive potential obtained through fitting, relative energy and structural similarity are taken as grading functions to evaluate the fitting every time, close result errors can be obtained by reducing energy errors, and accordingly, a better fitting effect is fulfilled.

D: separation point perturbation and sample perturbation are generated through a differential evolution algorithm; 20 times of fitting in each generation (20 individuals) are ranked according to a grading evaluation value, and a difference between an optimal individual vector and other individual vectors is acquired by taking the division points and the supplementary sample points as one vector to generate a vector in a perturbation direction; perturbation in multiple perturbation directions is performed on other vectors to generate new division points and supplementary samples; if the new division points are beyond a border, a division point which meets a condition is randomly generated; and if the new supplementary samples are not within a train set, one of the supplementary samples contained in the train set is randomly extracted to serve as a new supplementary sample; and E: iterating step C-D till errors are converged.

Embodiment 2

Due to the fact that equilibrium positions of different bond types as well as energy and force are mainly adopted, while only a small quantity of sample points is adopted for assisting the fitting in a fitting process, the information of the equilibrium positions is primarily retained, and the weights of the equilibrium positions are approximately equal, so that the problem of disequilibrium of bond types in fitting is solved. For example, C—O needs fitting of repulsive energy within an interval of 2.0-4.6 Bohr, and at least 52 train samples are needed according to a uniform division interval of 0.05. As shown in FIG. 2, related parameters of repulsive potentials on equilibrium positions are smaller, and parameters on a starting point are larger, so that the fitting weight is gradually reduced from the starting point to an end point, and a fitting result trends to obtain a close equilibrium position; when bond types are different, bond types of the repulsive potentials with larger related parameters are more reliable correspondingly; in C—O, C=O bonds are described more accurately; if spline fitting is directly adopted, the distances of the C=O bonds and C—O bonds are 1.18 A and 1.25 A; however, in experiments, the distances of the C=O bonds and the C—O bonds are 1.23 A and 1.43 A.

As the vicinity of the equilibrium positions is primarily concerned by researchers in research of chemistry, materials, biology and the like, parameters of only two equilibrium points are actually adopted in a C—O fitting process; in order to obtain a more accurate fitting effect, samples close to 1-2 equilibrium points are adopted as supplementary samples, the fitting weight of multiple bond types is equilibrated, for example, after one time of fitting, the distances of C=O bonds and C—O bonds can reach 1.22 A and 1.42 A and are obviously superior to those of direct spline fitting.

Embodiment 3

Due to the fact that a linear equation is used for fitting, the fitting of multiple repulsive potentials can be taken into one linear equation together to be realized, so that the problem of parameter compatibility is solved; for example, as for spline fitting of C—O, firstly, all parameters of H—H, C—C, O—O, O—H and C—H need to be prepared; any absent parameters should be prepared to continue the spline fitting; besides, the parameters have the problem of coupling compatibility, for example, the action of H—H causes calculation of values of C—O train samples, which in turns influences the fitting of C—O, and in this case, in order to obtain compatible parameters, multiple sets of parameters have to repeatedly adjusted to determine a final repulsive potential parameter, and consequentially, the efficiency is low. According to the method, the linear equations are adopted for fitting, and parameters of H—H and C—O can be taken into one set of linear equations to be solved, so that parameters compatible to two atomic pairs are obtained at a time.

According to the invention, automatic fitting of repulsive potentials is realized by means of differential evolution algorithm and a database. An equilibrium bond length is adjusted to be reasonable by spline fitting through repeated testing and fitting weight adjustment for changing related points, manual operation is frequent, and the effect is generally unsatisfactory. Fitting adopted by the invention solves the problems of bond type equilibrium and parameter compatibility, and realizes fine adjustment of repulsive potentials by adjusting division points through the differential evolution algorithm, thereby further improving the fitting effect. In conclusion, the invention realizes the automatic fitting of the repulsive potentials.

The above content is a detailed description of the invention in combination with optimal embodiments; however, specific embodiments of the invention are not limited to the above description. Those ordinarily skilled in this filed are permitted to make various simple deductions or replacements without deviating the conception of the invention, and these simple deductions or the replacements are ought to be within the protection scope of the invention.

What is claimed is:

1. A method for automatically and efficiently fitting repulsive potentials through DFTB, comprising the following steps:
   (1) obtaining a molecule containing an atomic pair, and performing a spacing scan on the atomic pair according to an acting interval of repulsive potentials;
   (2) performing a high-accuracy energy calculation on a structure obtained through the spacing scan;
   (3) performing a difference calculation on obtained energy to obtain second-order derivatives of force and energy;
   (4) saving a value of the energy obtained by calculating the structure through the high-accuracy energy calculation as well as the second-order derivatives of force and energy into a database;
   (5) acquiring a difference between a result obtained through the high-accuracy energy calculation and energy without a repulsive potential as well as force and second-order derivatives of energy which are obtained by calculating the structure to obtain target values of the repulsive potentials;

(6) performing spline interpolation according to an atomic spacing and the target values of repulsive potential energy to obtain multiple splines, and transforming separated samples into a continuous spline;

(7) setting a mean position between equilibrium position points as a splice point, determining end point energy as 0.0 according to a position of a fitting end point, and splicing multiple splines at a division point in a reverse order from the fitting end point to obtain new train energy data;

(8) constructing a train set pool by choosing two points closest to a starting point and an end point of a target repulsive potential as well as the equilibrium position points as necessary sample points and by choosing 2-3 sample points close to a fitting starting point as supplementary sample points; and (9) performing fitting by a singular value decomposition scheme to obtain an initial parameter, then performing quadratic fitting on an initial repulsive potential to transform the initial repulsive potential into a standard repulsive potential, wherein in step (9), a curve of the initial repulsive potential is defined as:

$$S_{ABi}(r) = \sum_{k=0}^{4} s_{ABik}(r - r_{ABi})^k,$$

wherein A and B are elements corresponding to atoms of the atomic pair, k is power of number, r is the atomic spacing, i is a division interval sequence corresponds to the atomic spacing, $s_{ABik}$ is a coefficient of $k^{th}$ polynomial in an $i^{th}$ interval, and $r_{ABi}$ is a starting point of the $i^{th}$ interval, corresponding repulsive energy:

$$E^{rep} = \sum_{a,b>a} V^{rep}_{ab}(r_{ab}) = \sum_{a,b>a} \sum_{k=0}^{4} s_{E_a E_b ik}(r_{ab} - r_{E_a E_b i})^k,$$

wherein a, b are atoms of the atomic pair, $E_a$ and $E_b$ are elements corresponding to a and b, $r_{ab}$ is the atomic spacing, $s_{E_a E_b ik}$ is the coefficient of $k^{th}$ polynomial in the $i^{th}$ interval, and $r_{E_a E_b i}$ is the starting point of the $i^{th}$ interval, force:

$$\left.\frac{dV^{rep}_{ab}}{dr}\right|_{r=r_{ab}} = \sum_{a,b>a} \sum_{k=0}^{4} k \times s_{E_a E_b ik}(r_{ab} - r_{E_a E_b i})^{k-1},$$

according to an expression of the initial repulsive potential, fitting is expressed as a form of a linear equation: M·s=b, wherein M is a matrix determined by a form of a multi-section polynomial, second-order continued derivable information on division points and sample point information, s is a vector determined by all parameters to be fitted, b is values of energy, a derivative and a second derivative which correspond to the second-order continued derivable information and the sample point information;

according to continued derivability and a fitted value of the repulsive potential, an equation is regulated as the following form:

$$\begin{bmatrix} M^{cont} \\ M^{fit} \end{bmatrix} \cdot s = \begin{bmatrix} 0 \\ b^{fit} \end{bmatrix},$$

wherein $M^{cont}$ is a matrix containing the second-order continued derivable information on the division points, $M^{fit}$ is a matrix containing the sample point information, $b^{fit}$ is vectors containing the values of energy, the derivative and the second derivative which correspond to the sample point information, the equation is transformed to obtain $M^{last} \cdot s^{expl} = b^{fit}$, wherein $M^{last}$ is a last fitting matrix arranged with $M^{cont}$ and $M^{fit}$, $s^{expl}$ is a partial vector of s which need fitted explicitly to $b^{fit}$.

2. The method according to claim 1, wherein in step (3), the difference calculation is performed on the obtained energy through the high-accuracy energy calculation to obtain the second-order derivatives of force and energy.

3. The method according to claim 2, wherein in step (4), the high-accuracy method is one of MP2, G3B3 and CCSD/CBS methods.

4. The method according to claim 1, wherein in step (4), the high-accuracy energy calculation is one of MP2, G3B3 and CCSD/CBS methods.

5. The method according to claim 1, wherein in step (5), the difference between the result obtained through the high-accuracy energy calculation and the energy without a repulsive potential as well as the second-order derivatives of force and energy which are obtained by calculating the structure through a procedure of DFTB calculation, namely DFTB+, is acquired to obtain corresponding values of the repulsive potentials.

6. The method according to claim 1, wherein in step (8), train sets and the division points are optimized through a differential evolution algorithm, wherein step (8) includes following steps:

A: initializing the division points and separation points by mean positions between the starting point and one equilibrium point, between one equilibrium point and one equilibrium point, and between one equilibrium point and the end point;

B: randomly extracting 1-2 supplementary samples from the train set pool according to a density of the samples and the division points to maintain at least one sample within a separation point interval, and performing transverse perturbation without going beyond the necessary samples on the division points to generate individuals;

C: fitting each said individual and validating an evaluation error, wherein the step of fitting each said individual comprises: fitting the initial repulsive potential and the target repulsive potential;

D: generating separation point perturbation and sample perturbation through the differential evolution algorithm; sequencing fitting in each generation according to a grading evaluation value, and acquiring a difference between an optimal individual vector and other individual vectors by taking the division points and the supplementary sample points as one vector to generate a vector in a perturbation direction; performing perturbation in multiple perturbation directions on other vectors to generate new division points and supplementary samples; if the new division points are beyond a border, randomly generating a division point which meets a condition; and if the new supplementary samples are not within a train set, randomly extracting one of the supplementary samples contained in the train set as a new supplementary sample; and E: iterating steps C-D till errors are converged.

7. The method according to claim 6, wherein in step A, at least one said division point is contained between one equilibrium point and one equilibrium point.

* * * * *